(12) United States Patent
Ciccolella et al.

(10) Patent No.: US 6,224,608 B1
(45) Date of Patent: May 1, 2001

(54) TISSUE HOLDING DEVICE AND METHOD

(75) Inventors: Michael Ciccolella, Lake Carmel, NY (US); Paul A. Matula, Danbury, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 08/072,654

(22) Filed: Jun. 3, 1993

Related U.S. Application Data (63) Continuation of application No. 07/565,626, filed on Aug. 10, 1990, now abandoned.

(51) Int. Cl.$^7$ ..................................................... A61F 11/00
(52) U.S. Cl. ........................... 606/108; 606/170; 606/185; 604/115; 604/117; 604/165.01; 604/274
(58) Field of Search .................................. 604/164, 165, 604/264, 175, 166, 117, 115, 239, 272–274; 606/108, 185, 73, 170, 175; 128/753, 754; 411/411

(56) References Cited

U.S. PATENT DOCUMENTS

| | | | | |
|---|---|---|---|---|
| 137,414 | * | 4/1873 | Burdick | 411/411 |
| 2,256,942 | | 9/1941 | Duffy | 604/274 |
| 3,241,554 | * | 3/1966 | Coanda | 604/105 |
| 3,726,522 | * | 4/1973 | Silberman | 272/84 |
| 3,750,667 | | 8/1973 | Pshenichny | 128/215 |
| 4,601,710 | | 7/1986 | Moll | 604/165 |
| 4,654,030 | | 3/1987 | Moll | 604/165 |
| 4,670,008 | * | 6/1987 | Von Albertini | 604/165 |
| 4,902,280 | | 2/1990 | Lander | 604/165 |
| 4,926,860 | * | 5/1990 | Stice et al. | 604/264 |
| 5,009,643 | * | 4/1991 | Reich et al. | 604/165 |

FOREIGN PATENT DOCUMENTS

0232600 * 8/1987 (EP) .

OTHER PUBLICATIONS

Instruction for Use, ENDOPATH Disposable Surgical Trocar and Sleeve, copyright Ethicon, Inc. 1989.
Auto Suture SURGIGRIP 5mm Disposable Sleeves, box with instructions for use, copyright 1990, United States Surgical Corporation.
Bone Screw Technical Information, Copyright Richards Manufacturing Co., Inc., 1980.

* cited by examiner

Primary Examiner—Ronald K. Stright, Jr.

(57) ABSTRACT

A tissue gripping thread configuration for securely positioning an elongated medical instrument relative to body tissue. The tissue gripping thread includes curved distal and proximal foot sections connected to a thread base, a curved distal thread surface extending from the distal foot section to a thread apex, and a proximal thread wall substantially perpendicular to the base surface extending from the proximal curved foot section to the thread apex. In the preferred embodiment the flank angle of the distal thread surface is substantially greater than the flank angle of the proximal thread wall. The preferred thread configuration reduces trauma to tissue during insertion and removal of an associated medical instrument while ensuring secure positioning of the instrument relative to tissue. Preferred thread dimensions and radii, as well as embodiments for associating the preferred thread configuration with a trocar device are disclosed.

11 Claims, 5 Drawing Sheets

TISSUE HOLDING DEVICE AND METHOD

This is a continuation of U.S. Ser. No. 07/565,626, filed Aug. 10, 1990 now abandoned.

TECHNICAL FIELD

The present invention relates to a device for retaining a medical instrument in engagement with body tissue and, more specifically, to an improved device for maintaining the desired positional relationship between a trocar tube and body tissue.

BACKGROUND AND OBJECTS OF THE INVENTION

Devices for holding medical instruments in penetrating relationship with body tissue are known. See, for example, U.S. Pat. No. 2,256,942 which discloses an instrument having a fluted or undulated surface for retaining the device in the walls of the bladder or viscus; U.S. Pat. No. 3,750,667 which discloses a device having a thread which serves to measure the depth of introduction of the device into osseous tissue; and U.S. Pat. No. 4,670,008 which discloses a high flux threaded needle for injecting or removing fluids from the body, the needle having a threaded portion to permit easy insertion of the needle and secure the device in the patient.

Threaded structures have also been applied to larger diameter trocars which are used for introducing viewing and surgical instruments into the body. Such trocars are shown and described in U.S. Pat. Nos. 4,601,710; 4,654,030, and 4,902,280. One commercially available trocar includes an integrally molded threaded portion for holding the trocar in the patient's skin. Another device provides a depth penetration indicator adjustable to a desired position along a trocar and including a threaded portion for holding the trocar in the patient's skin.

The present invention provides an improved thread configuration for holding a medical instrument associated therewith in a desired position relative to a patient's body, specifically the patient's skin. The thread configuration of the present invention facilitates insertion and removal of the anchoring device into the patient's skin with decreased tissue trauma, and also provides sufficient holding power to maintain the medical instrument in the desired position.

SUMMARY OF THE INVENTION

In accordance with the invention a tissue gripping thread configuration is provided having a base surface, a distal foot section connected to the base surface, a sloping distal thread surface extending from the distal foot section to a thread apex, a proximal foot section connected to the base surface, and a proximal thread end wall substantially perpendicular to the base surface extending from the proximal foot section to the thread apex. In order to provide optimum insertion and tissue holding characteristics, the flank angle of the distal sloping surface is substantially greater than the flank angle of the proximal thread wall surface. Preferably, the distal thread surface, thread apex and the distal and proximal foot sections are curved to further optimize insertion and removal force and minimize tissue trauma. Preferred radii of curvature are disclosed. In the preferred embodiment the proximal thread wall has a flank angle of about 10°. That is, the proximal wall is inclined from a configuration perpendicular to the base surface by an angle of about 10°.

The tissue gripping thread may be associated in any suitable manner with a medical instrument having an elongated portion to engage and secure the instrument relative to body tissue. The thread configuration preferably is disposed in a helical arrangement surrounding at least part of the instrument elongated portion. In a preferred application, the threads are disposed on a cylindrical trocar guide tube. In one embodiment a trocar penetration depth indicator and positioning device is provided with an elongated cylindrical section configured to surround a trocar guide tube with the helical threads disposed outwardly of the guide tube outer surface. In this embodiment, the penetration depth indicator and positioning device is secured to the guide tube in the desired position and the trocar is inserted into body tissue. The threads are brought into contact with the body tissue and rotated so that the threads engage the body tissue and hold the trocar in position. In an alternative embodiment the elongated guide tube surrounding structure is integral with and extends from the guide tube housing. In this embodiment the entire guide tube housing is rotated to engage the body tissue.

The preferred thread configuration reduces tissue trauma during insertion into and removal from tissue while ensuring sufficient tissue gripping capability to prevent inadvertent removal of the instrument from the tissue.

It will be understood by those skilled in the art that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the present invention, and together with the description, serve to explain the principles of the invention.

DETAILED DESCRIPTION OF THE PREFERRED EMBODIMENTS

Referring now to the drawings, the present invention provides a tissue gripping thread 10 associated with a medical instrument for holding the medical instrument in a desired position relative to body tissue.

Figure 1:
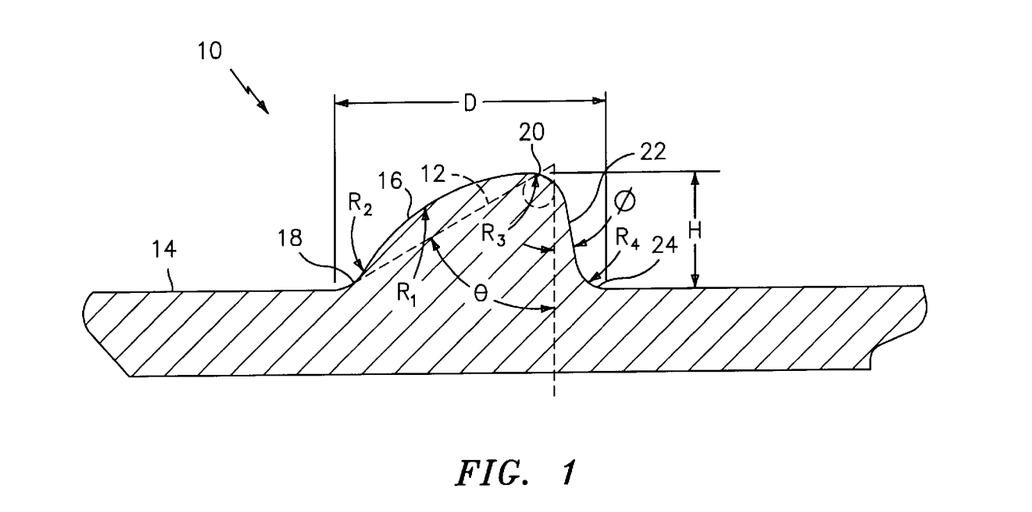
FIG. 1 is a cross section view of the preferred thread configuration constructed in accordance with the present invention.

As shown in FIG. 1, a cross-section view of the thread configuration of the present invention, thread 12 is mounted to a base surface 14 associated with a medical instrument. Thread 12 has a distal sloping surface 16 extending from a curved distal foot region 18 to a curved thread apex 20 disposed radially outward of base surface 14. Distal sloping surface 16 preferably is curved and has a radius $R_1$ in the range of about 0.07 to 0.09 inches, and most preferably has a radius of about 0.08 inches. Curved distal foot region 18 is connected to and extends from base surface 14 to join sloping surface 16 to the base surface. Curved distal foot region 18 should have a radius $R_2$ in the range of about 0.01 to 0.03 inches, and preferably has a radius of about 0.02 inches. Thread 12 also has a proximal end wall 22 substantially perpendicular to base surface 14 extending from a proximal foot region 24 to thread apex 20. Thread apex 20 preferably defines a curved surface connecting distal sloping surface 16 to proximal end wall 22. The curve of thread apex 20 preferably defines a radius $R_3$ of about 0.01 inches. Proximal foot region 24 joins proximal end wall 22 to base surface 14, and preferably is a curved surface defined by a radius $R_4$ of about 0.01 inches. The total longitudinal thread length D is measured from the point where distal curved foot region 18 joins base surface 14 to the point where proximal curved foot region 24 joins base surface 14. Thread length D and thread height H are selected so as to provide, in combination with the curved surfaces described above, optimum entry and removal force with minimum tissue trauma, and sufficient holding power to retain the associated medical instrument in the desired position. For tissue such as skin, the thread length D should be about 0.10 to 0.11 inches and the thread height H should be about 0.08 to 0.09 inches. It has also been found that for skin tissue the optimum longitudinal thread spacing "S" along base surface 14 (see FIG. 5A) should be about 0.275 to 0.300 inches, and most preferably is about 0.285 inches. The respective radii of distal curved foot section 18, distal thread surface 16, thread apex 20 and proximal curved foot section 24 also optimize entry and removal forces and minimize tissue trauma.

In accordance with the invention, the flank angles of the distal sloping thread surface and the proximal end wall are unequal. As shown in FIG. 1, the distal sloping surface flank angle θ is defined as the angle between the vertical and the slope of the distal thread surface. The slope of the distal thread surface can be determined by completing the circle defined by the radius $R_3$ and drawing a tangent from the inner side of curved surface 18 to the opposite side of the hypothetical circle. Such a tangent is shown in phantom in FIG. 1. As will be appreciated, the slope of surface 16 could also be directly determined by drawing a tangent to surface 16. Similarly, the proximal end wall flank angle ø is defined as the angle between the vertical and the slope of the proximal end wall, as shown. In accordance with the invention the distal surface flank angle θ is substantially greater than the proximal end wall flank angle ø in order to provide for ease of introduction into tissue while assuring sufficient tissue gripping force to hold the medical instrument in place. In the preferred embodiment the ratio of the flank angles θ:¥ is about 6:1. By way of example only, where ø equals about 10 degrees ø would be about 60 degrees.

Figure 2:
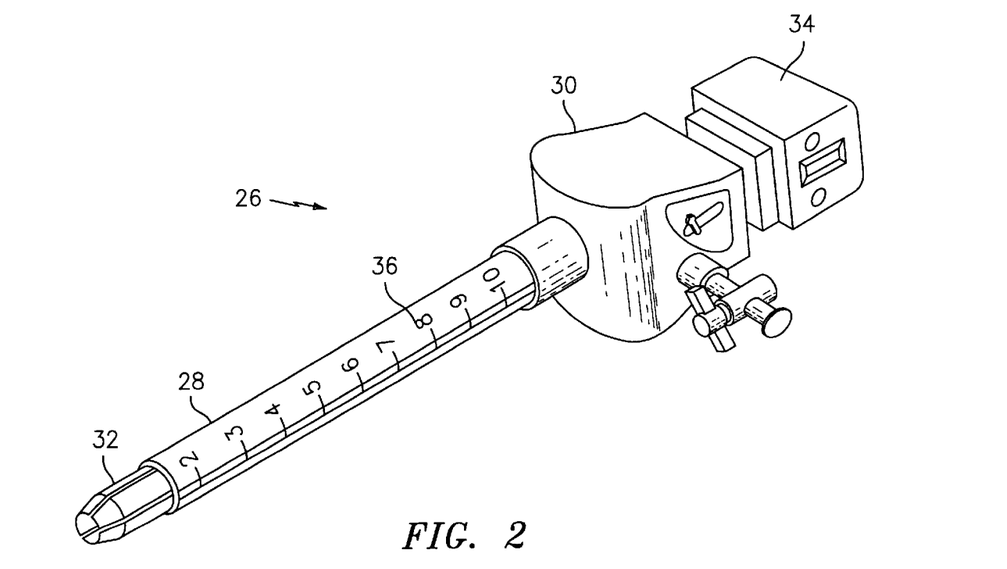
FIG. 2 is a perspective view of a trocar to which the preferred thread configuration may find application.

The specific thread configuration and dimensions discribed above are particularly suited for securely positioning a trocar relative to a patient's skin. FIG. 2 illustrates a known trocar device 26 having a guide tube 28 extending distally from a guide tube housing 30, and a stylet protective shield tube 32 slidably mounted within guide tube 28 and supported by a stylet housing 34. Stylet housing 34 also supports a sharp-tipped stylet (not shown) disposed within protective tube 32. Generally, protective tube 32 is spring biased and locked in the extended position shown in FIG. 2 prior to use. In order to use the trocar, guide tube housing 30 and stylet housing 34 are urged together to unlock protective tube 32, and the tip of the trocar is pressed against the patient's body. As the trocar tip is pressed against the body, the protective tube is urged proximally within the guide tube to reveal the sharp stylet for penetration of the body wall. After penetration, the protective tube returns to the extended locked position shown in FIG. 2. In this manner, the guide tube is inserted into the patient's body and may be maneuvered to the desired point. The guide tube, with the stylet and protective tube removed, provides access for viewing and/or performing surgery within the body without a traditional incision. The guide tube and guide tube housing at all times provide a seal between the penetrated body cavity and the external atmosphere, and guide tube 28 preferably is provided with penetration depth indicia, shown in the form of a graduated scale 36, for indicating the penetration depth of the guide tube into the body.

The thread configuration of the present invention is intended to be associated with guide tube 28, also known as a cannula, to hold the guide tube relative to body tissue. Of course, it is immaterial to the present invention how the guide tube is introduced into the body or whether the device includes a safety shield.

Figure 3:
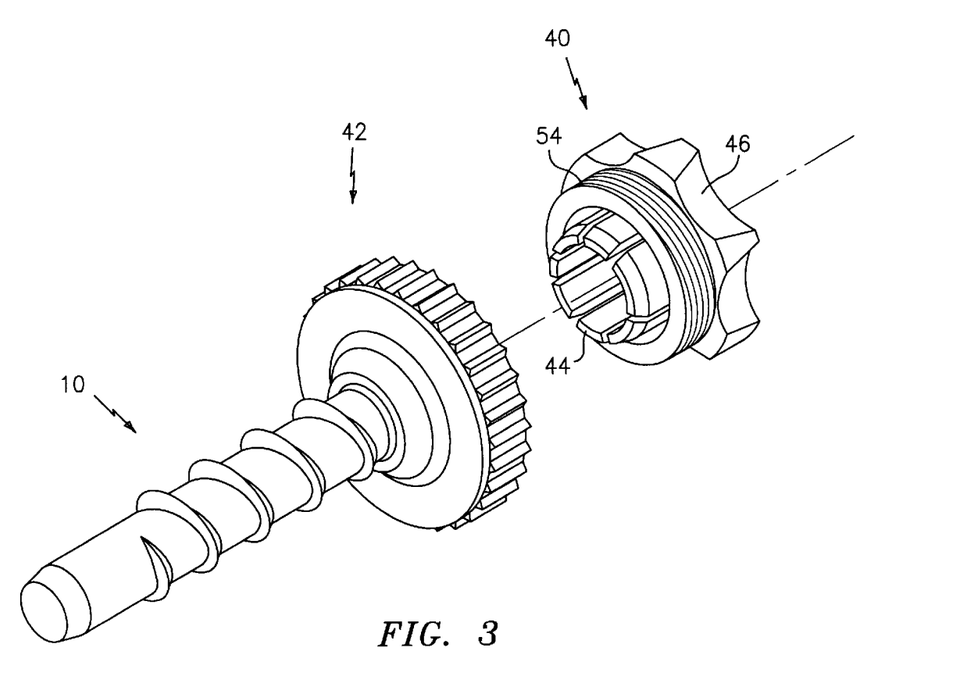
FIG. 3 is a perspective view of a trocar penetration depth indicator and positioning device incorporating the thread configuration of the present invention.

Referring now to FIG. 3, the preferred mode for associating thread 10 with guide tube 28 is shown in the form of a position depth indicator and positioning device. The position depth indicator and positioning device includes a first, inner housing 40 and a second, outer housing 42. The first and second housings have axially aligned apertures to receive guide tube 28. The inner and outer housings rotatably engage to assume an unlocked position wherein the depth indicator and positioning device may slidably be urged along guide tube 28 to a desired position. After the desired position has been attained, the inner and outer housings are rotated relative to one another so that a camming surface on the outer housing constricts a plurality of gripping fingers 44 on the inner housing to frictionally engage and grasp the guide tube, thereby preventing further sliding motion of the depth indicator and positioning device relative to the guide tube.

Figure 4A:
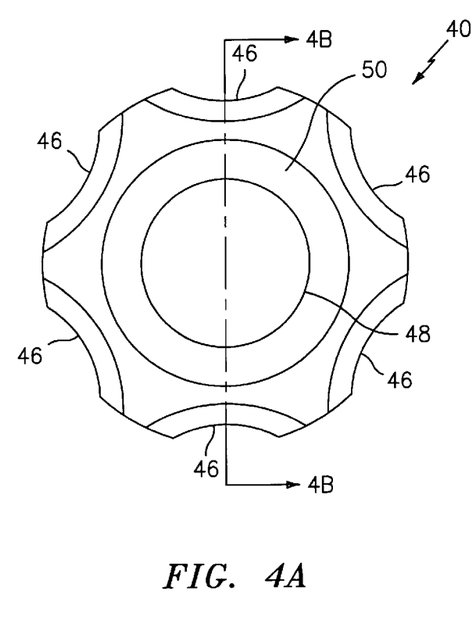
FIG. 4A is a proximal end view of the inner housing of the positioning device shown in FIG. 3.
Figure 4B:
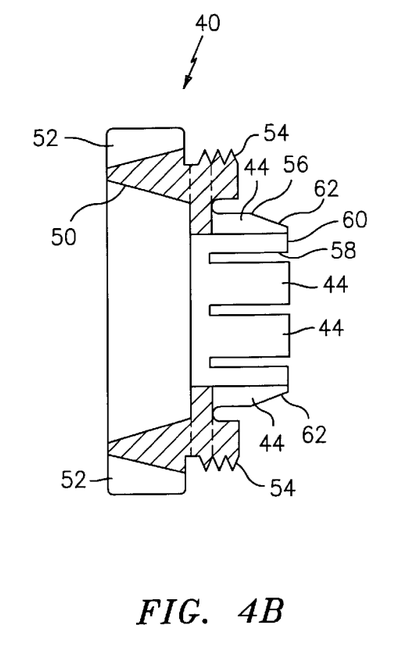
FIG. 4B is a cross section view of the inner housing taken along lines 4—4 of FIG. 4A.
Figure 4C:
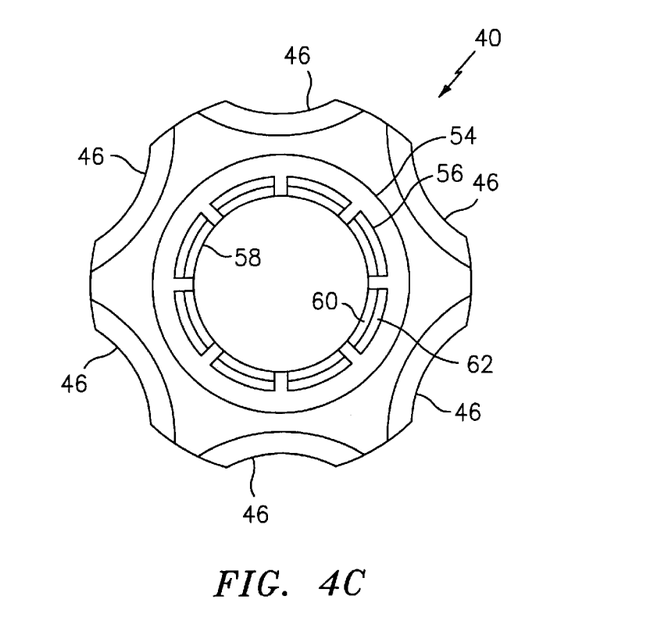
FIG. 4C is a distal end view of the inner housing of FIG. 4A.

FIG. 4A is a proximal end view of inner housing 40 showing finger accommodating depressions 46 disposed on the outer circumference of the inner housing. Also shown are a central aperture 48 and a nesting area 50 for accommodating the guide tube and a portion of the guide tube housing, respectively. FIG. 4B is a cross-section view of inner housing 40 taken along lines 4—4 of FIG. 4A. As there illustrated, the inner housing is generally cylindrical and includes a gripping portion 52 integral with finger depressions 46. The inner housing also has an outwardly facing threaded section 54 to engage an outer housing threaded section, and a number of longitudinally extending gripping fingers 44 for frictionally gripping the trocar guide tube under constriction of the outer housing. Each gripping finger has an outer surface 56, an inner surface 58 and a distal end surface 60. Preferably, a distally inwardly inclined gripping finger camming surface 62 is provided between the outer gripping finger surface 56 and distal end surface 60. As explained more fully below, gripping finger camming surface 62 engages an outer housing camming surface to ensure uniform, inward radial constriction of the gripping fingers to grip the guide tube. Nesting area 50 is illustrated in FIG. 4B as an inclined surface of distally decreasing diameter. The increased proximal open area obtained by the inclined surface of nesting area 50 accommodates a portion of the guide tube housing (see FIG. 2). Of course, the nesting area could also take other forms, such as an area of uniform enlarged diameter sufficient to accommodate the guide tube housing. FIG. 4C, a distal end view of inner housing 40, illustrates the arrangement of the gripping fingers. As shown, the inner surface 58 of each gripping finger is curved to conform to the radius of curvature of the guide tube. FIG. 4C also illustrates the preferred arrangement of eight gripping fingers. The number and specific arrangement of gripping fingers are not critical, but the preferred arrangement of a plurality of gripping fingers having concave inner surfaces advantageously distributes gripping forces about the circumferential area of contact with the trocar guide tube.

Figure 5A:
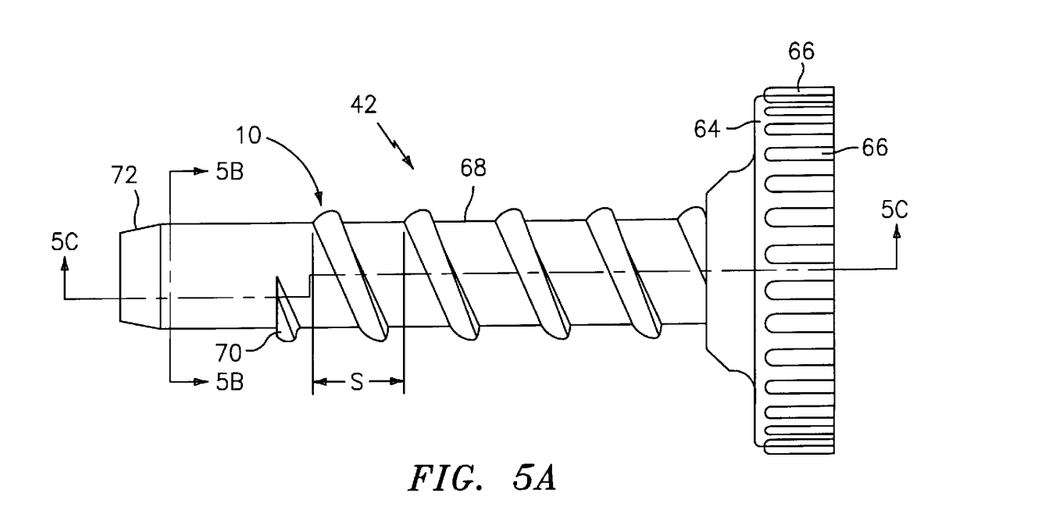
FIG. 5A is a side elevation view of the outer housing of the positioning device illustrated in FIG. 3.

FIG. 5A is a side elevaton view of outer housing 42 showing an outer housing gripping portion 64 having radially extending ribs 66 to facilitate manipulation of the second housing. Outer housing 42 includes a distally extending guide tube surrounding section 68 which is substantially cylindrical and is configured to receive guide tube 28 therethrough. As shown, section 68 defines the base surface from which thread pattern 10 radially extends in a helical pattern. Thread 10 includes a distal, thread initiating portion 70 which increases gradually in height from the surface of guide tube surrounding section 68 until full thread height is acheived. As also shown in FIG. 5A, threads 12 are evenly spaced along the base surface defined by guide tube surrounding section 68, the spacing being defined by thread spacing "S". "S" represents the on-center thread spacing which preferably is about 0.285 inches. Guide tube surrounding section 68 further includes a distal, inwardly sloping section 72 to facilitate insertion of section 68 into body tissue. Preferably, sloping section 72 and the elongated surface of guide tube surrounding section 68 define an angle of about 10 degrees.

Figure 5B:
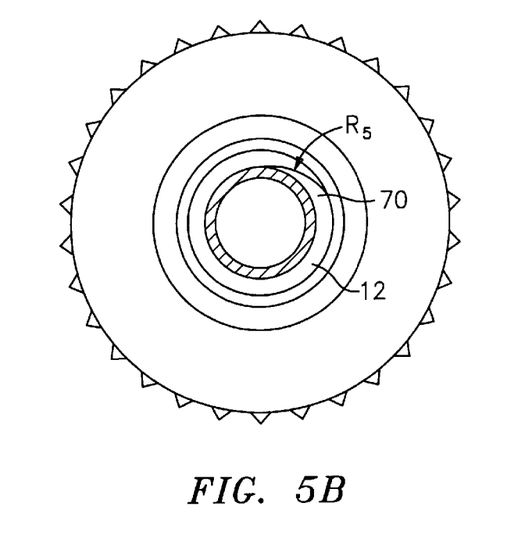
FIG. 5B is a distal cross section view of the outer housing taken along lines 5B—5B of FIG. 5A.

FIG. 5B is a distal cross-section view of outer housing 42 taken along lines 5B—5B of FIG. 5A. As there shown, thread initiating portion 70 commences at the surface of cylindrical section 68 and gradually increases in height until the full height of thread 12 is acheived. Preferably, the radius of curvature $R_S$ of thread initiating section 70 shown in FIG. 5B is about 0.2 inches so as to appropriately blend the start of the thread to the base surface.

Figure 5C:
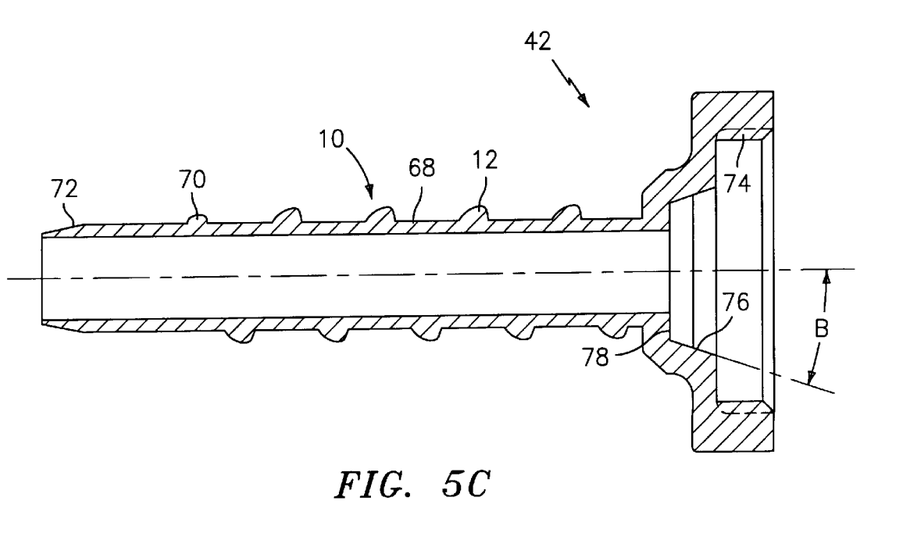
FIG. 5C is a cross section view of the outer housing taken along lines 5C—5C of FIG. 5A.

FIG. 5C is a cross-section view of the outer housing taken perpendicular to the plane of FIG. 5A along lines 5C—5C of FIG. 5A, showing threads 12 disposed along the elongate surface of guide tube surrounding section 68. Thread initiating section 70 is shown having a partial thread height. As shown in FIG. 5C, outer housing 42 has a substantially open center having a minimum diameter defined by the diameter of the cylindrical guide tube receiving section 68. By way of example only, for a 5 mm trocar section 68 has an inner diameter of about 0.250 to 0.275 inches, and preferably is in the range of about 0.260 to 0.265 inches. The outer diameter of section 68 may appropriately be 0.325 to 0.330 inches. Those skilled in the art will recognize that other dimensions will be required to accomodate trocar guide tubes of different diameters. Outer housing 42 includes an inwardly facing outer housing threaded section 74 and a distally inwardly inclined camming surface 76. In the preferred embodiment, camming surface 76 defines an angle B of about 20 to 25° relative to the longitudinal axis of the second housing. Gripping finger camming surface 62 (see FIG. 4B) is similarly angled to interact with camming surface 76 such that camming surface 76 exerts radially inward force on the gripping fingers as the camming surfaces are brought together.

By way of example only, inner and outer housings 40, 42 may be constructed, as by molding, of a glass filled acetal or polycarbonate. In the preferred embodiment the outer housing is constructed of glass-filled acetal and inner housing is constructed of polycarbonate. The preferred acetal material is available from LNP Division of ICI America Inc. under the trade specification KFL 4023, and the preferred polycarbonate material is available from General Electric Company under the trade name LEXAN. The preferred acetal-polycarbonate arrangement reduces binding at the threaded engagement of the inner and outer housing threaded sections. of course, the same result may be obtained by constructing the outer housing of polycarbonate and the inner housing of acetal, but an acetal inner housing may slide on a metal cannula or guide tube.

In use, the trocar penetration depth indicator and positioning device of FIG. 3 is mounted onto the trocar guide tube. The depth indicator and positioning device preferably is mounted to the guide tube disposed in an unlocked position with the inner and outer housing loosely engaged by threaded sections 54, 74. In the unlocked position the device may be moved longitudinally along the guide tube to the desired penetration depth position. Once disposed in the desired position, the inner and outer housings are rotatably tightened together, so that the penetration depth indicator and positioning device assumes a locked, tightened position firmly and immovably grasping the guide tube. As will be understood, rotatably tightening the inner and outer housings by engagement of threaded sections 54, 74 causes the inner and outer housings to be longitudinally drawn together. As the housings are drawn together, outer housing camming surface 76 engages gripping finger camming surfaces 62 to exert radially inward force on gripping fingers 44 to securely grasp the outer surface of guide tube 28. Advantageously, the plurality of gripping fingers conforming to the guide tube surface uniformly distributes substantial frictional gripping force over virtually the entire guide tube surface. Remarkably, the present invention develops sufficient gripping force to withstand substantial force, on the order of about 25–30 pounds. However, because the gripping force is not concentrated over a small area, there is no danger of damaging the structural configuration of the guide tube.

In order to obtain these desirable features, the inner housing should be configured and dimensioned so that gripping fingers 44 define an opening having a diameter slightly larger than the outer diameter of the corresponding guide tube when the gripping fingers are not constricted by the outer housing. Similarly, in order to obtain sufficient gripping force, the gripping fingers should be constricted by the outer housing so as to define an opening having a diameter conforming to the outer diameter of the guide tube. Advantageously, the maximum constriction of the gripping fingers may be limited by limiting the travel of the threaded sections of the inner and outer housings. In this regard, a vertical stop wall 78 is provided in outer housing 42 to abut gripping finger surface 60 (see FIG. 4B) when the desired gripping force is established. In order to achieve the desired gripping action without overtightening, it is contemplated that the maximum tightened position of the threaded inner and outer housings should constrict the gripping fingers to a maximum constricted position defining an aperture having a diameter slightly smaller than the outer diameter of the guide tube. By way of example only, a standard 10 millimeter trocar has a nominal inner diameter of about 10 millimeters and a nominal outer diameter of about 10.3 millimeters. Accordingly, a depth indicator and positioning device of the present invention for use with a 10 mm trocar should be constructed so that the inner housing gripping fingers define an opening slightly larger than 10.3 millimeters in diameter when not constricted by the outer housing, i.e., on the order of about 10.4 or 10.5 millimeters. Conversely, the maximum constriction of the gripping fingers by the outer housing should define an aperture slightly less than about 10.3 millimeters in diameter, such as from about 9.8 to 10.2 millimeters. Of course, the maximum constricted position would actually be achieved only in the absence of a guide tube, but so defining a maximum constricted position makes it impossible to overtighten the depth indicator to cause deformation of the guide tube. Such close tolerances also assure that the gaseous seal between the body cavity will be preserved. It will be understood by those of ordinary skill in the art that these principles and considerations also apply to depth indicator and positioning devices to be used with different size trocars.

After the positioning device has been secured to the guide tube and the trocar has been inserted into the patient's body, inwardly sloping section 72 is urged into the trocar incision until thread initiating portion 70 engages the skin. The positioning device then is rotated counterclockwise relative to the view of FIG. 5B so that thread 10 engages and becomes enveloped in the patient's skin. It is contemplated that the same result can be obtained by rotating the entire trocar relative to the patient's skin with the depth indicator and positioning device in the locked position gripping the guide tube. Advantageously, the positioning device engaged with the skin thereafter may be unlocked to adjust the position of the guide tube relative to the patient's skin, with the positioning device being re-locked relative to the guide tube after a new guide tube position has been selected. To remove the positioning device, the device merely is rotated clockwise relative to the view shown in FIG. 5B to disengage thread 10 from the patient's skin. The preferred thread configuration advantageously reduces trauma to the skin during insertion and removal and provides sufficient resistance to withdrawal of the trocar from the patient's skin so as to securely hold the trocar in the desired position.

Figure 6:
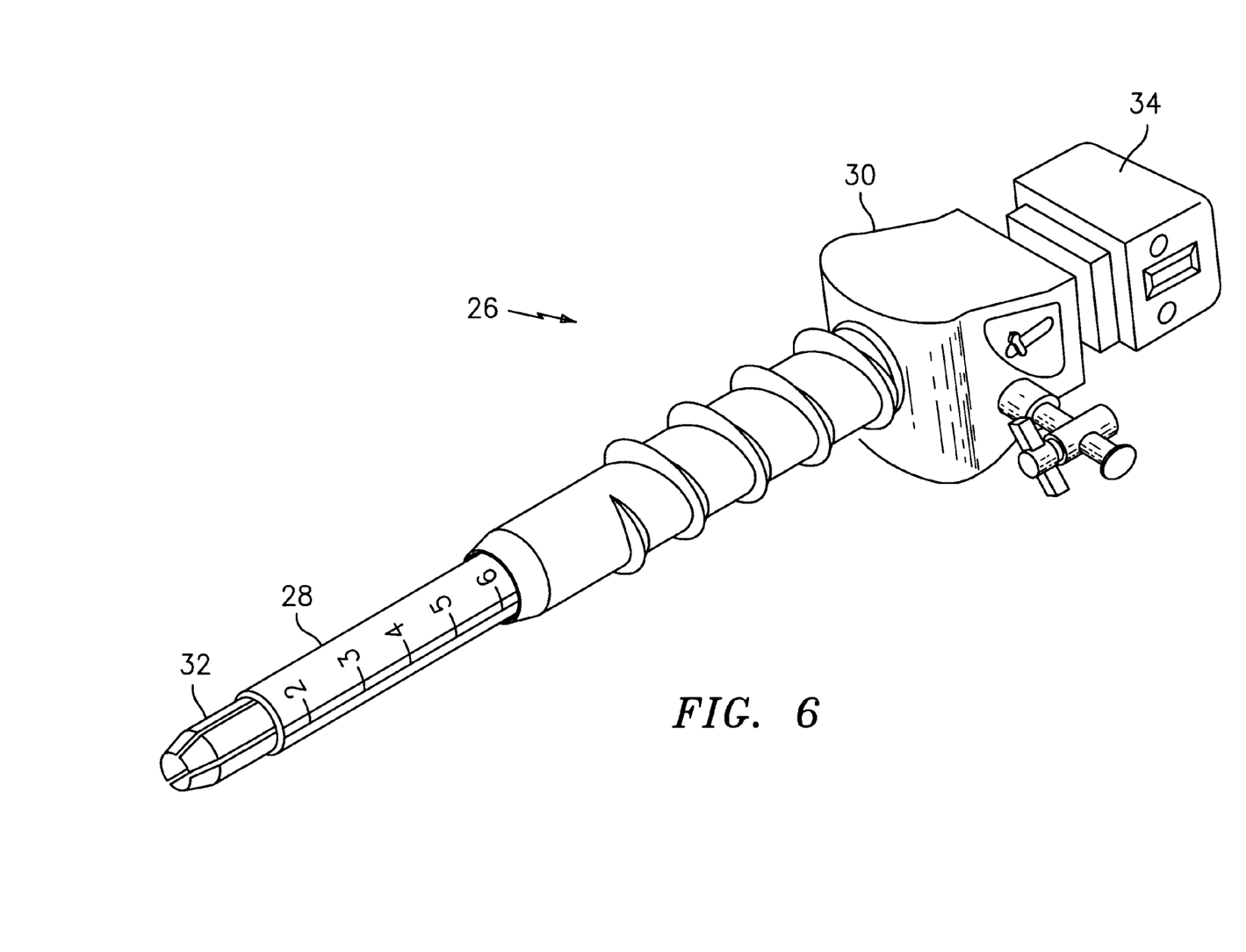
FIG. 6 is a perspective view of an alternative embodiment of the invention, illustrating the thread configuration of the present invention integral with the guide tube housing.

In an alternative embodiment shown in FIG. 6, the elongated guide tube surrounding section 68 is integrally formed with and extends from guide tube housing 30 to support thread 10. This embodiment is less preferred because the position of thread 10 along guide tube 28 cannot be adjusted. However, this alternative construction may be entirely satisfactory where full insertion of the trocar is expected, and illustrates another means of associating thread 10 with guide tube 28. In this embodiment thread 10 is engaged with the patient's skin by rotating the guide tube housing relative to the patient's skin.

To the extent not already indicated, it will be understood by those of ordinary skill in the art that any one of the various specific embodiments herein described and illustrated may be further modified to incorporate features shown in other of the specific embodiments, as desired. By way of example only, it is contemplated that a multiple start thread configuration may be employed to further ease insertion of the threads into tissue. It also will be understood that the finger gripping depressions may be disposed on the inner housing and the gripping projections on the outer housing, rather than as shown herein. It is also contemplated that the housing distal to the guide tube housing could comprise the inner housing with gripping fingers, in which case the proximal housing would preferably include a nesting area. Furthermore, the shape, configuration and construction materials for the penetration depth indicator and positioning device may be varied, as appropriate.

The invention in its broader aspects therefore is not limited to the specific embodiments herein shown and described, but departures may be made therefrom within the scope of the accompanying claims, without departing from the principles of the invention and without sacrificing its chief advantages.

What is claimed is:

1. A trocar positioning device comprising:
  (i) first housing means configured and dimensioned to slidably engage a trocar guide tube, said first housing means having guide tube gripping means for selectively gripping the guide tube; and
  (ii) second housing means configured and dimensioned to engage said first housing means to cause said gripping means to grip the guide tube and prevent movement of said trocar positioning device relative to the guide tube, said second housing means having tissue engaging thread means for engaging body tissue and securing the position of the trocar positioning device relative thereto, said thread means having a base, a distal surface extending from said second housing to a thread apex, and a proximal thread wall extending from the second housing to said thread apex;
  wherein a distal read surface flank angle is defined by the angle between a vertical line perpendicular to said base extending through said thread apex and a line extending from said distal thread based surface to said thread apex, and a proximal end wall flank angle is defined by the angle between a vertical line perpendicular to said base extending through said thread apex and said proximal end wall;

wherein said flank angle of said distal thread surface is greater than said flank angle of said proximal end wall, at a ratio of about 6 to about 1 respectively:

wherein said distal thread surface has a radius of curvature of about 0.07 to about 0.09 inches.

2. The trocar positioning device of claim 1 wherein said second housing means includes a substantially cylindrical elongate section extending distally from said second housing means, said thread means being disposed on the outer surface of said elongate section.

3. The trocar positioning device of claim 2 wherein said substantially cylindrical elongate section has a sloping distal surface.

4. The trocar positioning device of claim 3 wherein said elongate section sloping distal surface defines an angle of about 10 degrees relative to said elongate section outer surface.

5. The trocar positioning device according to claim 4 wherein said proximal thread wall flank angle is about 10 degrees.

6. The trocar positioning device of claim 1 wherein said first housing means has a first engaging portion, a plurality of guide tube gripping fingers, and a substantially cylindrical first housing aperture configured and dimensioned to receive the guide tube with said guide tube gripping fingers extending longitudinally to and surrounding the guide tube, and said second housing means has a second engaging portion configured and dimensioned to engage said first engaging portion, a second housing means camming surface, and a second housing means aperture extending axially therethrough and aligned with said first housing means aperture to receive the guide tube, said first and second housing means assuming a first, unlocked position with said first and second housing means axially slidable along the guide tube, and a second, locked position wherein said second housing means camming surface exerts radially inward force upon said gripping fingers, such that said gripping fingers frictionally engage said guide tube to prevent axial sliding movement of said first and second housings relative to the guide tube.

7. The trocar positioning device of claim 6 wherein said first and second engaging portions further comprise mutually engaging threaded sections.

8. The trocar positioning device of claim 1 wherein said threaded apex has a radiused surface having a radius of curvature of about 0.01 inches.

9. The trocar positioning device of claim 1 wherein said proximal end wall flank angle is approximately 10 degrees.

10. The trocar positioning device of claim 1 wherein said threads are longitudinally spaced apart on center along said base by a distance of about 0.275 to about 0.3 inches.

11. The trocar positioning device of claim 1 wherein said thread has a height measured from said base to said thread apex in the range of about 0.08 to about 0.09 inches.

* * * * *